(12) United States Patent
Järnström et al.

(10) Patent No.: US 6,254,883 B1
(45) Date of Patent: *Jul. 3, 2001

(54) COMPOSITION FOR TRANSDERMAL DELIVERY OF DRUGS

(75) Inventors: Risto Järnström, Loviisa; Jouni Hirvonen, Kuopio, both of (FI)

(73) Assignee: Novagent Oy, Kauniainen (FI)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,333
(22) PCT Filed: Jan. 27, 1997
(86) PCT No.: PCT/FI97/00039
§ 371 Date: Jul. 7, 1998
§ 102(e) Date: Jul. 7, 1998
(87) PCT Pub. No.: WO97/27844
PCT Pub. Date: Aug. 7, 1997

(30) Foreign Application Priority Data

Jan. 30, 1996 (FI) .................................................. 960435
Jun. 12, 1996 (FI) .................................................. 962450

(51) Int. Cl.⁷ ............................................................ A61K 9/70
(52) U.S. Cl. ........................... 424/449; 424/448; 602/41; 604/20; 604/890.1
(58) Field of Search .................................. 424/449, 448; 604/890.1, 20; 602/41

(56) References Cited

U.S. PATENT DOCUMENTS

| | | | |
|---|---|---|---|
| 1,967,927 | 7/1934 | Deutsch | 174/89 |
| 4,032,452 | 6/1977 | Davis | 210/243 |
| 4,585,652 | 4/1986 | Miller et al. | 424/83 |
| 4,731,049 | 3/1988 | Parsi | 604/20 |
| 5,098,417 | 3/1992 | Yamazaki et al. | 604/304 |
| 5,162,042 | 11/1992 | Gyory et al. | 604/20 |
| 5,603,955 | 2/1997 | Gehrke et al. | 424/484 |
| 5,894,021 | 4/1999 | Okabe et al. | 424/449 |

FOREIGN PATENT DOCUMENTS

| | | |
|---|---|---|
| 0 195 643 A3 | 9/1986 | (EP) . |
| 925030 | 11/1992 | (FI) . |
| 95774 | 12/1995 | (FI) . |
| WO 90/03825 | 4/1990 | (WO) . |
| WO 92/15365 | 9/1992 | (WO) . |
| WO 94/08572 | 4/1994 | (WO) . |
| WO 96/10441 | 4/1996 | (WO) . |

OTHER PUBLICATIONS

Chien et al., "Development of Transdermal Controlled Release Drug Delivery Systems: An Overview," 1 *Transdermal Delivery of Drugs* 81–100 (1987).

Baker et al., "Materials Selection for Transdermal Delivery Systems," *Transdermal Drug Delivery, Developmental Issues and Research Initiatives* 293–311 (1989).

Sathyan et al., "Transdermal delivery of tacrine," 114 *Int. J. Pharm* 75–83 (1995) (Abstract only).*

Moriearty, "Transdermal Delivery of Cholinesterase Inhibitors," 4 *CNS Drugs* 323–334 (1995).

Primary Examiner—Michael C. Williamson
(74) Attorney, Agent, or Firm—James C. Lydon

(57) ABSTRACT

A pharmaceutical composition for the controlled transdermal delivery of a drug containing a combination of a drug and an ion exchanger group to a carrier, and a pharmaceutically acceptable salt that is able to control the release of the drug from the ion exchanger, in which the carrier is a textile fiber. According to a preferred embodiment the drug is tacrine or its pharmaceutically acceptable salt.

10 Claims, 7 Drawing Sheets

COMPOSITION FOR TRANSDERMAL DELIVERY OF DRUGS

This invention relates to a novel composition for controlled release of a drug in transdermal administration.

BACKGROUND OF THE INVENTION

The publications and other materials used herein to illuminate the background of the invention, and in particular, cases to provide additional details respecting the practice, are incorporated by reference.

Transdermal delivery is a feasible alternative route of drug administration for many drugs. Drugs whose daily dose is 20–30 mg or less, are potential candidates for transdermal drug delivery (Guy and Hadgraft 1987, Guy and Hadgraft 1989).

Transdermal administration of therapeutically active agents is usually accomplished by incorporating the drug into a transdermal delivery device which is able to control the delivery rate of the drug. According to one alternative the transdermal device comprises a backing layer, an adhesive layer and a matrix layer preferably made of a polymer material in which the drug is dispersed. The rate of which the drug is released from the device is here controlled by the polymer matrix. Another kind of transdermal device is the reservoir system comprising a) a drug impermeable backing layer, b) an adhesive layer, c) a drug permeable membrane sealed to one side of the backing layer as to define a drug reservoir compartment there between, and d) a drug or composition thereof within said drug reservoir. In this case the drug in the reservoir is usually in liquid or gel form. The drug permeable membrane controls the rate at which the drug is delivered to the skin.

U.S. Pat. No. 4,692,462 describes a composition and method for controlled transdermal delivery based on the use of a ion exchange resin loaded with the drug to be administered. This drug-loaded ion exchange resin is, together with a salt that is able to release the drug from the ion exchange resin, mixed with a gel-forming vehicle and incorporated in a device having a cavity, an adhesive layer and a backing layer.

SUMMARY OF THE INVENTION

The object of this invention is to provide a transdermal delivery composition which combine the features of controlled drug release and simple device construction.

The invention thus concerns a pharmaceutical composition for the controlled transdermal delivery of a drug comprising a combination of a drug and a ion exchanger group grafted to a carrier, and a pharmaceutically acceptable salt that is able to control the release of the drug from the ion exchanger. According to the invention the carrier is a textile fiber.

DETAILED DESCRIPTION OF THE INVENTION

Figure 1:
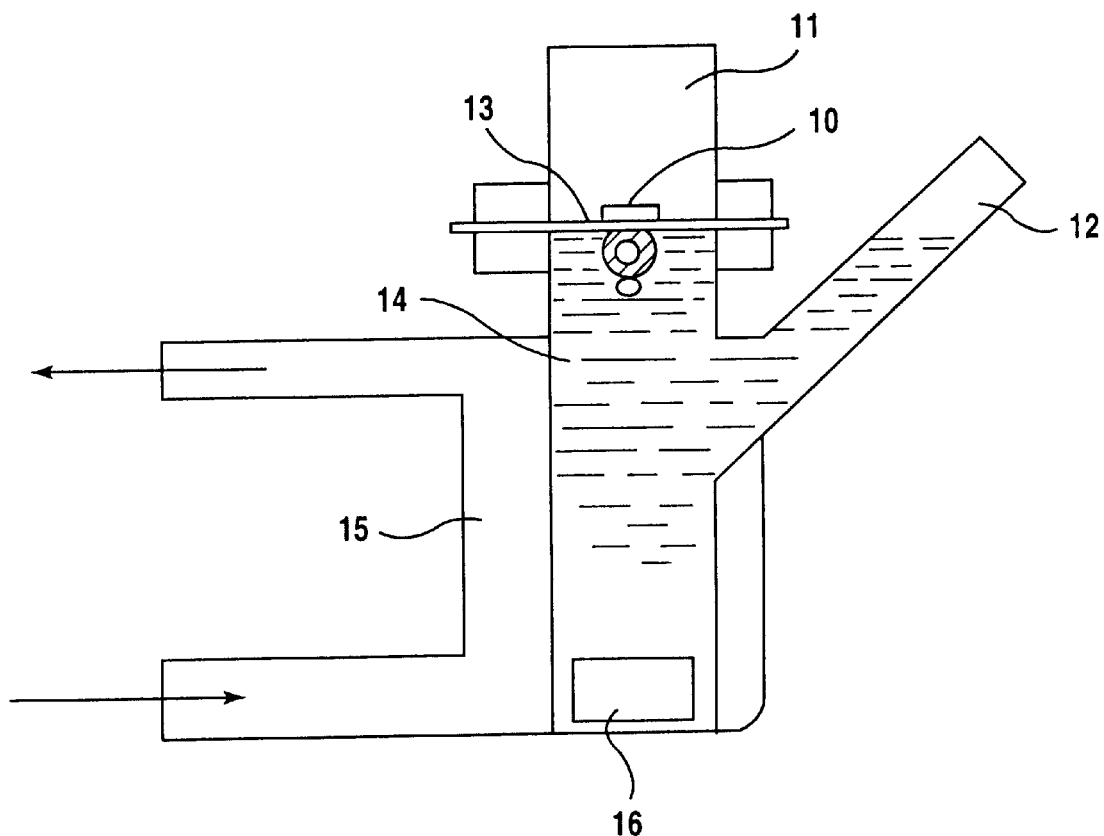
FIG. 1 shows the apparatus used in the test of the drug delivery rate.

Suitable fibers for use in this invention are any pharmaceutically acceptable textile fibers of native or synthetic origin. Examples of such fibers are wool, cotton, flax fibers and fibers of cellulose or its derivatives, polyethylene, polypropylene, polystyrene, polyamide fibers and carbon fibers.

Said fibers can be grafted with positive functional groups such as $-N^+(CH_3)_3$ (trimethylammonium), $-NH^+(CH_3)_2$ (dimethylammonium), or the like to give fibers having the ability to bind and release negative groups (anions), i.e. to give anionic exchangers. If the fibers are grafted with negative functional groups such as $-COOH$ (carboxylic) or $-SO^-_3$ (sulphonic), cationic exhangers are obtained.

The choice of the functional group depends on the properties of the drug to be administered, the desired loading and the desirable administration rate. The amount of functional groups grafted onto the fiber affects the loading capacity of the fiber.

The use of fibers grafted with suitable ion exchanger group possesses a considerable advantage over the use of ion exhange resins with respect to the kinetic properties. The loading and delivery of the active substance is much faster from a fiber than from a resin because the contact between the functional ion exchanger group is much better if said functional group is attached to a fiber than to a resin. The disadvantages of the resin are due to 1) great dimensions of the resin sphere compared to the cross section of a fiber, and 2) the cross-linking of the polymer in the resin restricts the motility of the functional group.

Suitable drugs to be administered by the anionic exchanger are typically acids having a $-COOH$ group such as acetylsalicylic acid, indomethacin, furosemide, acetaminophen, prostaglandins and the like. Drugs that can be administered by a cationic exchanger are basic compounds such as clonidine, dopamine, chlorpromazine, benzodiazepines, beta-blockers such as propranolol etc., selegiline and nicotine.

Examples of suitable salts for the release of the drug from the ion exchanger are sodium chloride, sodium phosphate (mono- or dibasic), zinc sulfate, magnesium chloride, calcium chloride, potassium chloride, sodium sulfate, magnesium acetate and sodium citrate.

A particularly preferred compound is the anticholinesterase inhibitor tacrine (9-amino-1,2,3,4-tetrahydroacridine) and its pharmaceutically acceptable salts (especially hydrochloride or hydrochloride monohydrate) which is used for treating the symptoms of mild to moderate Alzheimer's disease (Sathyan et al., 1995). Molecular weight of tacrine is 198,27 and partition coefficient of tacrine (Log K) is 3,30. Tacrine (-HCl) is soluble in water and at physiological pH it is assumed to carry a positive charge.

Tacrine appears to undergo extensive first-pass metabolism and is rapidly cleared from the systemic circulation.

The most important pharmacokinetic parameters of tacrine are short elimination half-life $T_{1/2}=1,4–3,6$ h, Clearance CL=150 l/h, and low peroral bioavailability (5–35%).

Based on these parameters, transdermal delivery of tacrine seems to be a realistic goal. After oral drug administration, the clinical tacrine concentration is about 5–30 ng/ml, above which unwanted side-effects are more likely to take place (Wagstaff and McTavish, 1994). By transdermal delivery of tacrine one may: 1. minimize first-pass metabolism in GI-tract and liver; 2. provide fairly constant blood levels for extended period of time, and 3. reduce the incidence of gastrointestinal side-effects and hepatotoxicity associated with peroral tacrine administration.

The salt is preferably encompassed in a gel which further is brought into contact with the textile fiber loaded with the drug. The drug-loaded textile fiber could be embedded in the gel. However, according to a preferable embodiment the gel is added to only one surface of a drug-loaded textile fiber sheet. The opposite surface of the textile sheet will rest against the patient's skin. The gel layer is preferably protected with a backing layer impermeable to the gel and the agents therein.

Suitable gel-forming substances are e.g. gelatin, agar, agarose, polyvinylalcohol, hydroxypropyl cellulose etc.

The transdermal composition according to this invention exhibits several advantageous features over the known reservoir devices. The textile bandage is simple in construction and convenient for the patient to wear. If necessary, big areas of the patient's skin can be exposed to drug delivery by the textile sheet. This composition would, for example, enable rapid administration of prostaglandine to necrotic body parts.

The following experiments demonstrate the invention.

EXPERIMENTS

Example 1

1. Introduction

Physicochemical properties of drugs e.g. molecular weight and oil/water partition properties affect the drug feasibility for transdermal administration. Generally, small lipophilic and uncharged molecules permeate skin more easily than large, polar and charged ones. At physiological pH human skin carries a net negative charge (Hirvonen 1994). The negative charge results from a greater number of carboxylic acid groups over amine moieties in the proteins on the skin surface, or from specific adsorption of ions on the skin surface. Thus, skin acts like an ion-exchange membrane and as a result cations may more easily permeate the skin than anions.

The aim of this study was to evaluate the suitability of a anionic ion-exchange fiber (AIEF) for transdermal drug delivery of ionic compounds by in vitro tests. Sodium salicylate (mw 160.1 g/mol), pKa 3.0 and 13.4) (Gynther 1993) was used as a model drug in the test.

2. Methods 2.1 Preparation of fiber discs containing sodium saliculate

In the experiments below a woven cloth was used comprising a cotton textile fiber (RAIEX AK II) in which tertiary amine groups ($-N^+(CH_3)_3$) had been grafted to the polysaccaride molecules. The surface weight of the cloth was 200 g/m². The thickness of the fiber was 30–40 µm, strength 10–20 kg s/mm², break stretch 15–40% and the ion exchanger capacity 3.3 mekv/g.

For release studies circular discs (diameter 25 mm) were cut from the above mentioned anionic ion-exchange fiber cloth. The fiber discs were washed by 5% $NaHCO_3$ solution in a dropfunnel until all chloride was exchanged (tested by silver nitrate in $HNO_3$ solution). Thereafter the discs were treated with 5% sodium salicylate solution. The discs containing salicylate were dried in 37° C.

2.2 Drug release in vitro

Drug release in vitro from the fiber discs at 37° C. was tested in Franz diffusion cells (Crown Glass Co. Inc., Somerville, N.J.) (FIG. 1). In the figure reference number 11 denotes the donor compartment, 14 receiver compartment, 15 thermostat, 16 stirring rod and 12 sample tube. The fiber discs 10 were placed in the diffusion cells so that one side of the anionic ion-exchange fiber was exposed to the dissolution medium. The dissolution medium was pH 7.4 phosphate buffer saline (PBS, 143 mM, $\mu=0.15$ ($\mu$=ionic strength)) in experiment 1 and pH 7.4 phosphate buffer (6 mM, $\mu=0.2$) in experiments 2 and 3. To assess the effect of the skin on drug release (experiment 3), a piece of epidermis 13 was placed between the fiber disc and buffer solution. At fixed times, samples of 250 µl were withdrawn and the drug concentration in the samples were determined by using HPLC (Beckman System Gold, Beckman Instrument, San Ramon, Calif.) with a Supelcosil LC-18-DB column (5 µm, 150×4.6 mm) (Supelco Inc., Rohm and Haab Co., Bellefonte, Pa.). The mobile phase was a binary mixture of methanol (40% v/v) and pH 7.0 phosphate buffer (60%). The detection wavelenght was 298 nm, and the flow rate of 1.0 ml/min, the retention time was 2.6 min.

3. Results

Figure 2:
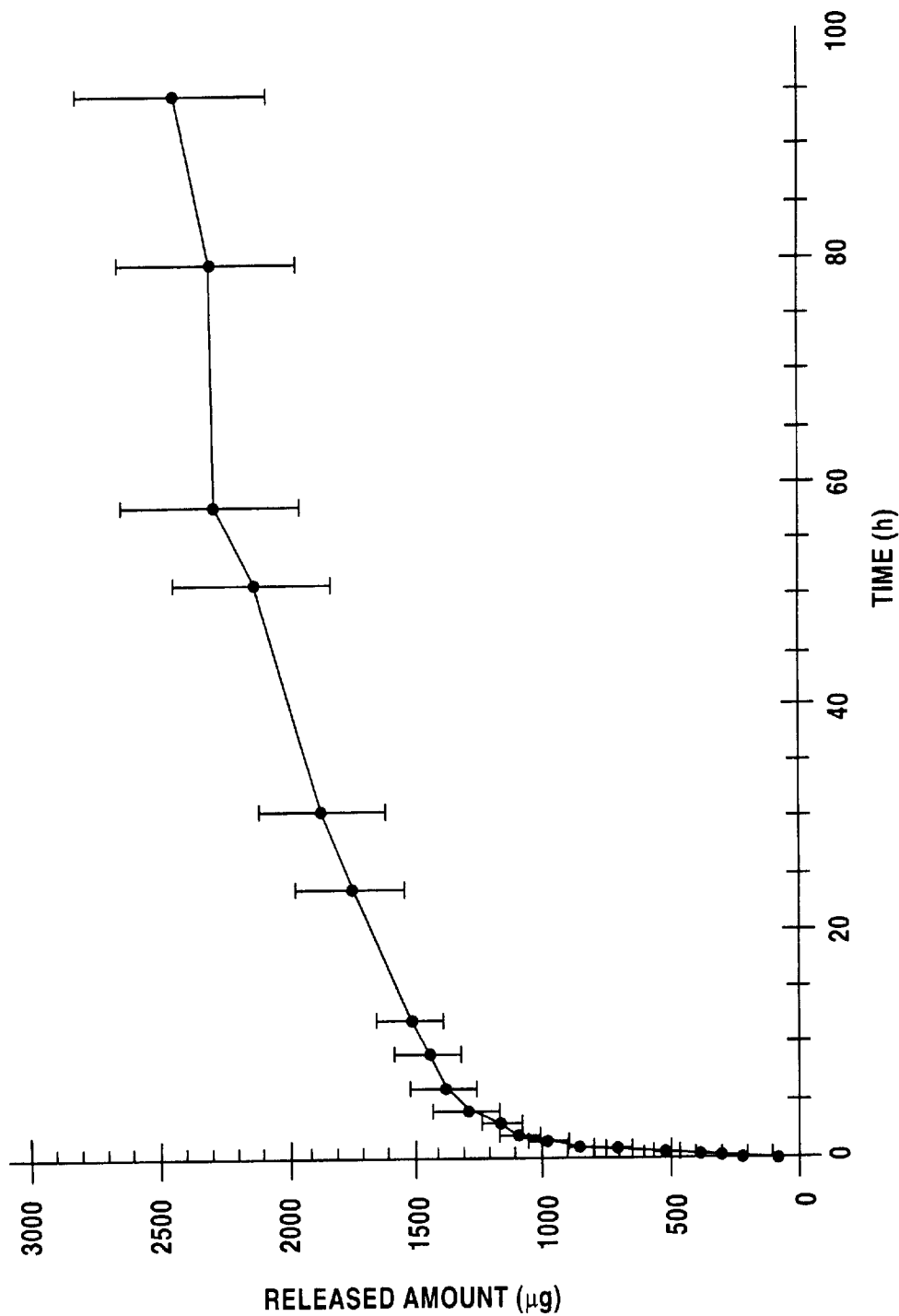
FIG. 2 shows the in vitro release of sodium salicylate from an anionic ion exchange textile fiber in PBS solution versus time (143 mM, $\mu$=0.15; Mean ±SE, N=7)
Figure 3:
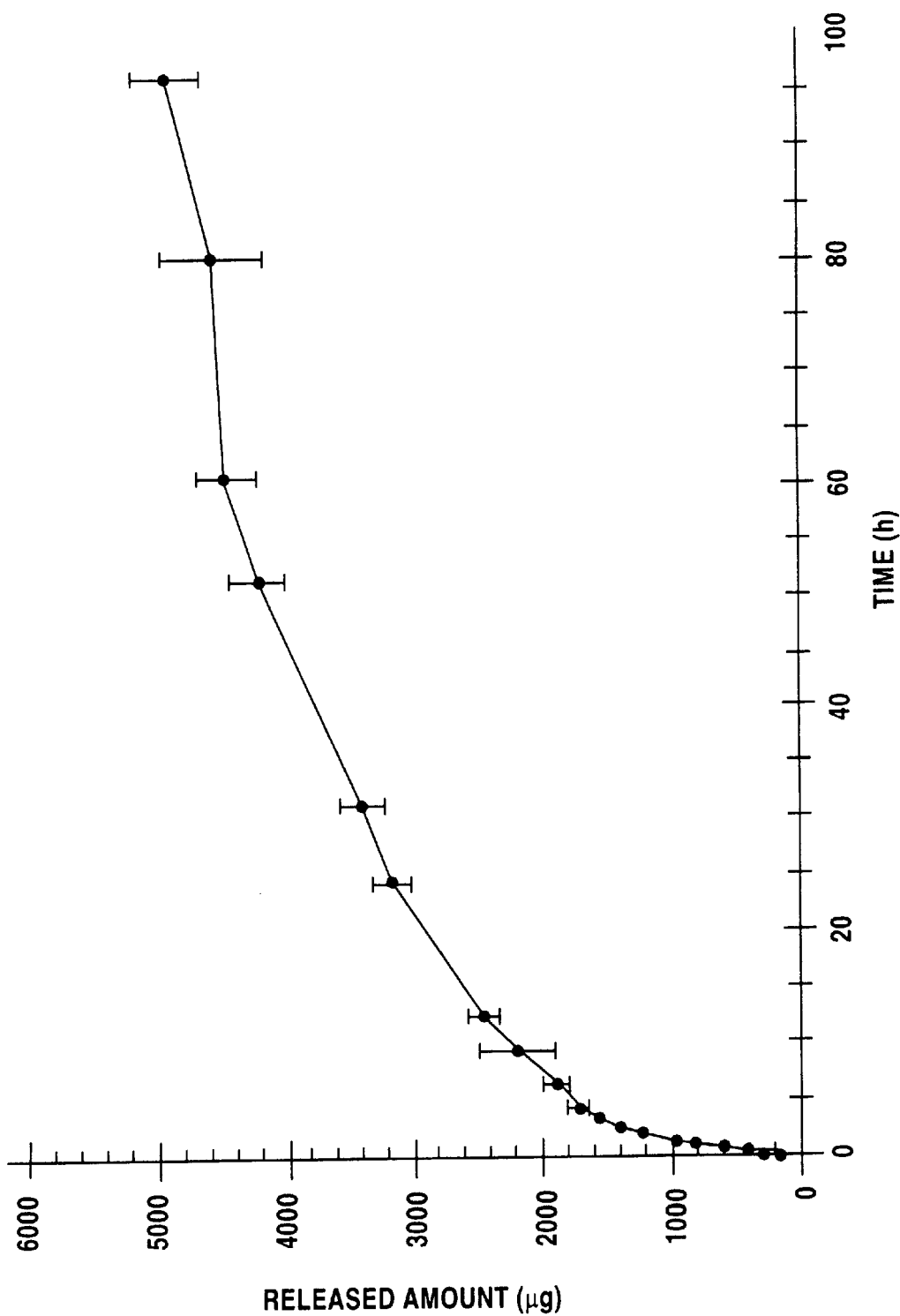
FIG. 3 shows the in vitro release of sodium salicylate from an anionic ion exchange textile fiber in phosphate buffer (pH 7.4) versus time (6 mM, $\mu$=0.2; Mean±SE, N=8)

In vitro release of salicylate from anionic ion-exchange fiber in PBS solution (143 mM, (143 mM, $\mu=0.5$) was very rapid in the beginning of the experiment 1 (about 350 µg/cm²) (FIG. 2). After initial burst (about<6 h) salicylate were released from the fiber discs very slowly but at a nearly constant rate (about 20–30 µg/h/cm²). Also in experiment 2 performed with phosphate buffer (6 mM, $\mu=0.20$) the burst effect was observed but during the constant release phase (about 50 h) the rate of salicylate release was higher (about 60 µg/h/cm²) than in PBS solution (FIG. 3).

Figure 4:
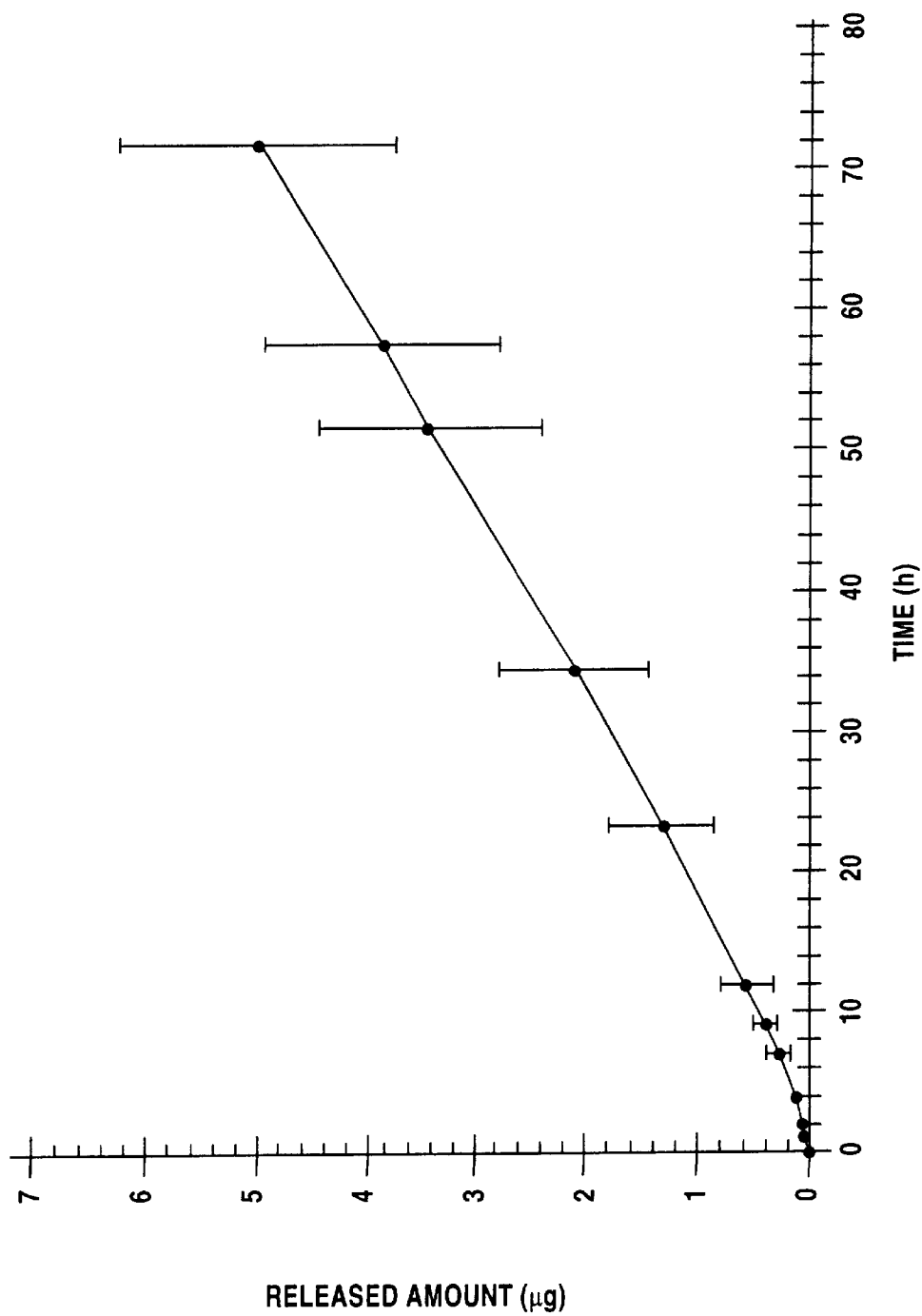
FIG. 4 shows the in vitro release of sodium salicylate from an anionic ion exchange textile fiber in phosphate buffer (pH 7.4) through skin versus time (6 mM, $\mu$=0.2; Mean±SE, N=8)

The release of salicylate from the discs was decreased markedly by effect of the skin in experiment 3. Salicylate release from anionic ion-exchange fiber was negligible (0.08 µg/h) and it followed zero-order kinetic after initial lag time (FIG. 4).

4. Discussion

The release rate and the released amount of salicylate were higher in phosphate buffer (6 mM, $\mu=0.20$) than in PBS solution (143 mM, $\mu=0.15$). This may be due to the better ion-exchange properties of phosphate buffer containing more NaCl. After initial burst, the drug was released at nearly constant rate (about 60 µg/h/cm²) for two days. This shows that with the tested anionic ion-exchange fiber it seems to be possible to control drug release.

Permeation of salicylate through epidermis was substantially slower (about 0.08 µg/h) than its release directly to the buffer solution. With skin, the burst effect disappeared. Lag time before steady state release was about 2 h. Thus, skin controls the transdermal salicylate delivery from the anionic ion-exchange fiber due to the poor skin permeability of anionic salicylate. This is supported to be the observation that the in vitro permeability of anionic salicylate through skin was about 0.34 µg/cm$^2$/h in pH 7.0 phosphate buffer (200 mM) containing 6.27 g/l NaCl when the concentration of drug in the donor solution was 50 µg/ml (Hirvonen 1994). Nevertheless, it is possible that the in vitro permeation through the skin might underestimate the potential total amount of bioavailable drug (Brain et al 1993). In vitro the contact between the skin and the anion exchange fiber may be poorer than in vivo.

5. Conclusions

With the tested anionic ion-exchange fiber it is possible to control the rate of salicylate release for several days in vitro. However, anionic salicylate is not the best model drug for the transdermal feasibility test of ion-exchange fibers due to the cation selective properties of the human skin. Cationic drugs are more suitable for transdermal administration (e.g. clonidine) and their skin permeability is also typically higher than anionic ones. It is therefore strongly believed still better results will be obtained for cationic ion-exchange fiber in the delivery of positive charged drugs.

Example 2

Preliminary test concerning transdermal delivery of tacrine hydrochloride monohydrate Tacrine hydrochloride monohydrate ($C_{13}H_{14}N_2 \times H_2O$, in the following abbreviated as $TNH_3Cl$), Sigma-Aldrich GmbH, was dissolved in water to give a 4.2% solution. An acidic fiber ion exchanger was treated with this solution, wherein the following reaction occurred:

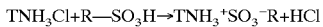

$TNH_3Cl + R-SO_3H \rightarrow TNH_3^+SO_3^-R + HCl$ wherein R is the back bone of the fiber ion exchanger (polypropylene). The fiber ion exchanger obtained contained 30 mg of tacrine per gram of fiber ion exchanger.

The ion exchange performance of this fiber ion-exchanger was tested in a Franz diffusion cell (see FIG. 1) to a buffered solution (pH=7), and t to blood through skin.

In both tests pharmacologically significant amounts of tacrine was delivered to the substrate.

Example 3

Transdermal release, permeation and delivery of tacrine

Methods

1. Preparation of fiber discs containing tacrine

To study tacrine release, circular discs (diameter 25 mm) were cut from the cationic ion-exchange fiber (Minsk, Belorussia). The cationic fiber discs were washed in 5% HCl solution in a dropfunnel until all sodium was exchanged. Thereafter the discs were treated with 5% tacrine (–HCl) solution. The discs containing tacrine were dried in 37 C. and each disc was analyzed to contain 16,7 mg of tacrine on the average. This relates to about 3,5% (mass/mass) tacrine content in the disc.

2. Tacrine release from the ion-exchange fiber

Drug release from the fiber discs was tested in vitro in Franz diffusion cells (Crown Glass Co., Somerville, N.J.) at 37 C. The fiber discs were placed in the diffusion cells so that one side of the cationic ion-exchange fiber was exposed to the dissolution medium (phosphate-buffer 6 mM, pH 7,4). Surface area of the fiber discs exposed to the buffer was 0,64 cm$^2$. Samples were withdrawn up to 72 h at fixed intervals and tacrine concentration in the samples was determined by HPLC (Beckman System Gold, Beckman Instruments Inc., San Ramon, Calif.). The column used was Supelcosil LC-18-DB (5 m, 150 mm×4,6 mm), and the mobile phase included 22% of acetonitrile, 1% of triethylamine, and 77% of phosphate buffer at pH 6,5. Detection wavelength was 240 nm and flow rate was 1,0 ml per min.

3. Tacrine permeation across human skin in vitro

Transdermal permeation of tacrine across human skin in vitro was studied with Side-by-Side -diffusion chambers (DC-100, Crown Glass Co., Somerville, N.J.) at room temperature (ca. 25 C.). Donor phase (3 ml) contained: 1,5% solution of tacrine (-HCl) in HEPES-buffer (pH 7,4), and 2. cationic ion exchange fiber with 3,5% of tacrine in HEPES-buffer. Samples were withdrawn up to 120 h at fixed intervals and tacrine concentration in the samples was determined by HPLC. Transdermal flux of tacrine (g/h per cm$^2$) across the skin was calculated using linear regression of the straight-line portion of drug permeation vs. time curve, and dividing by the surface area of the skin (0,64 cm$^2$).

Results

1. Fiber discs containing tacrine

Figure 5:
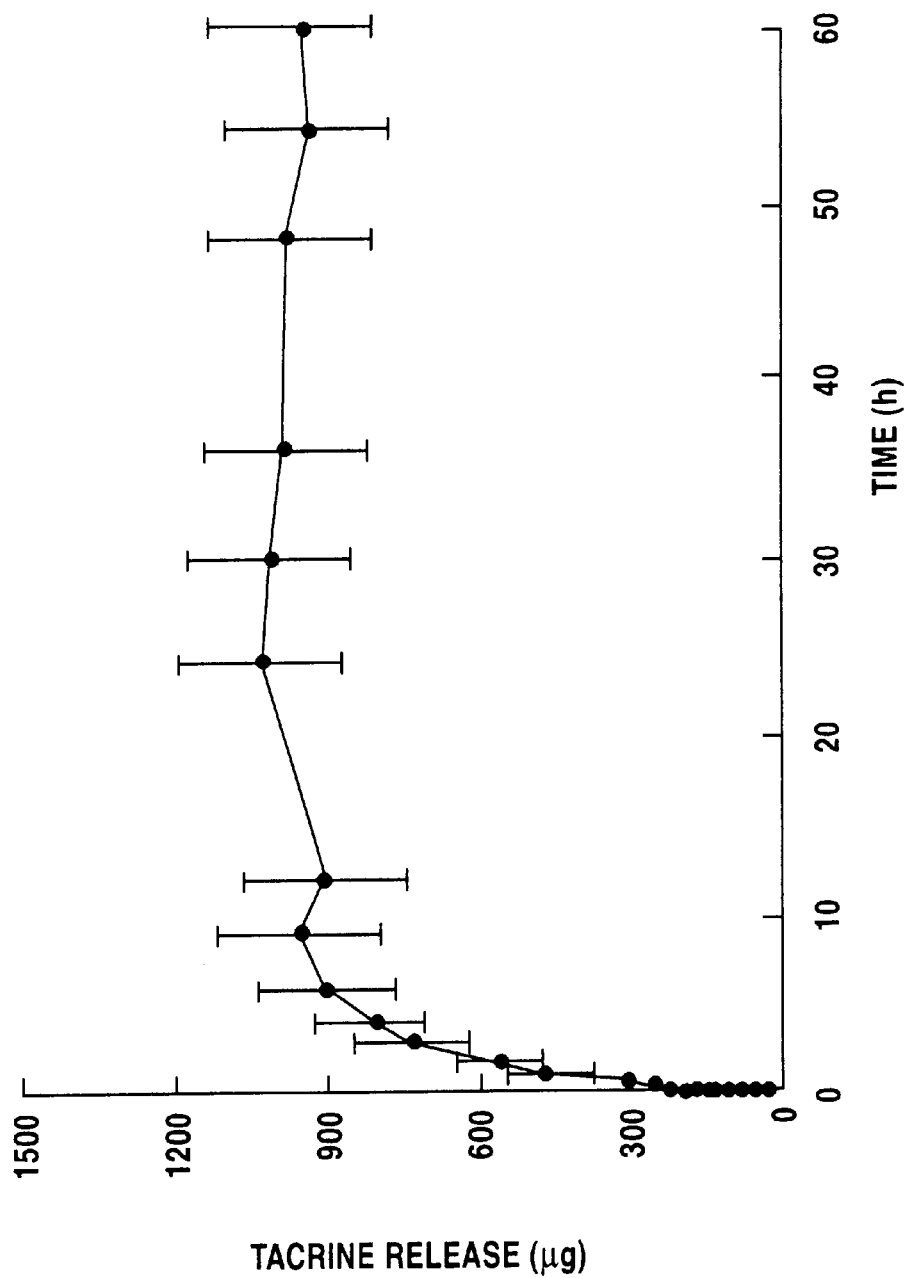
FIG. 5 shows the in vitro release of tacrine from a cationic ion-exchange fiber at pH 7.4. Average±SD, N=4.

Positively charged tacrine reacts chemically with the negative groups in the cationic ion exchange fiber. However, release of tacrine from the cationic ion-exchange fiber was very rapid in the beginning of the experiment (FIG. 5). After initial burst of about 6–12 h, 50% of tacrine was released from the fiber, whereafter further drug release was prevented by the reached equilibrium of tacrine in the buffer and the ion-exchange fiber. Tacrine release rate from the cationic ion-exchange fiber during the first 10 hours was about 375 g/h per cm$^2$. Therefore, cationic ion-exchange fiber seems very suitable material for a drug reservoir that can release tacrine in a controlled fashion.

2. Tacrine permeation across human skin in vitro

Figure 6:
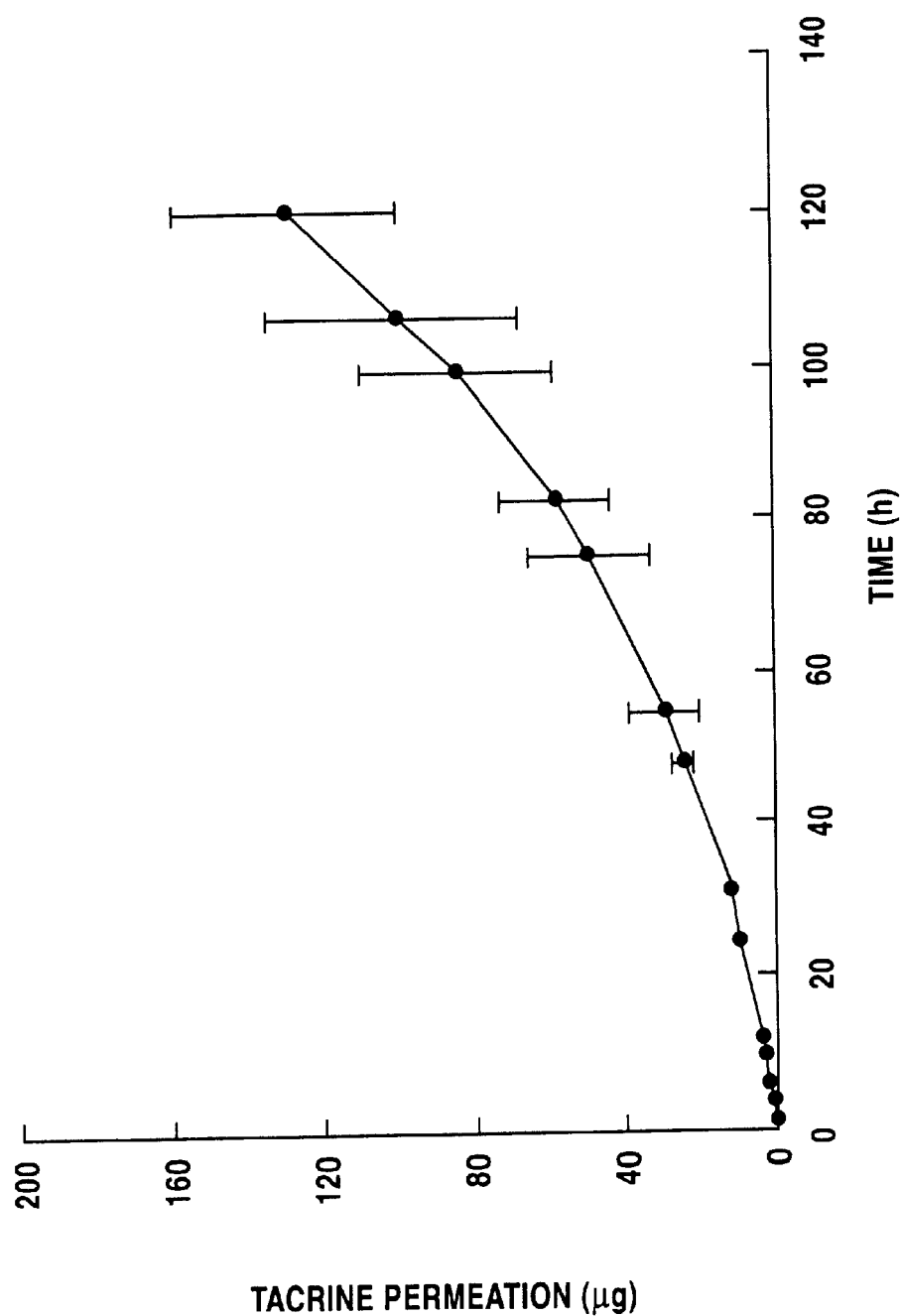
FIG. 6 shows tacrine permeation across human skin from 5 % solution in vitro. Average±SD, N=5.
Figure 7:
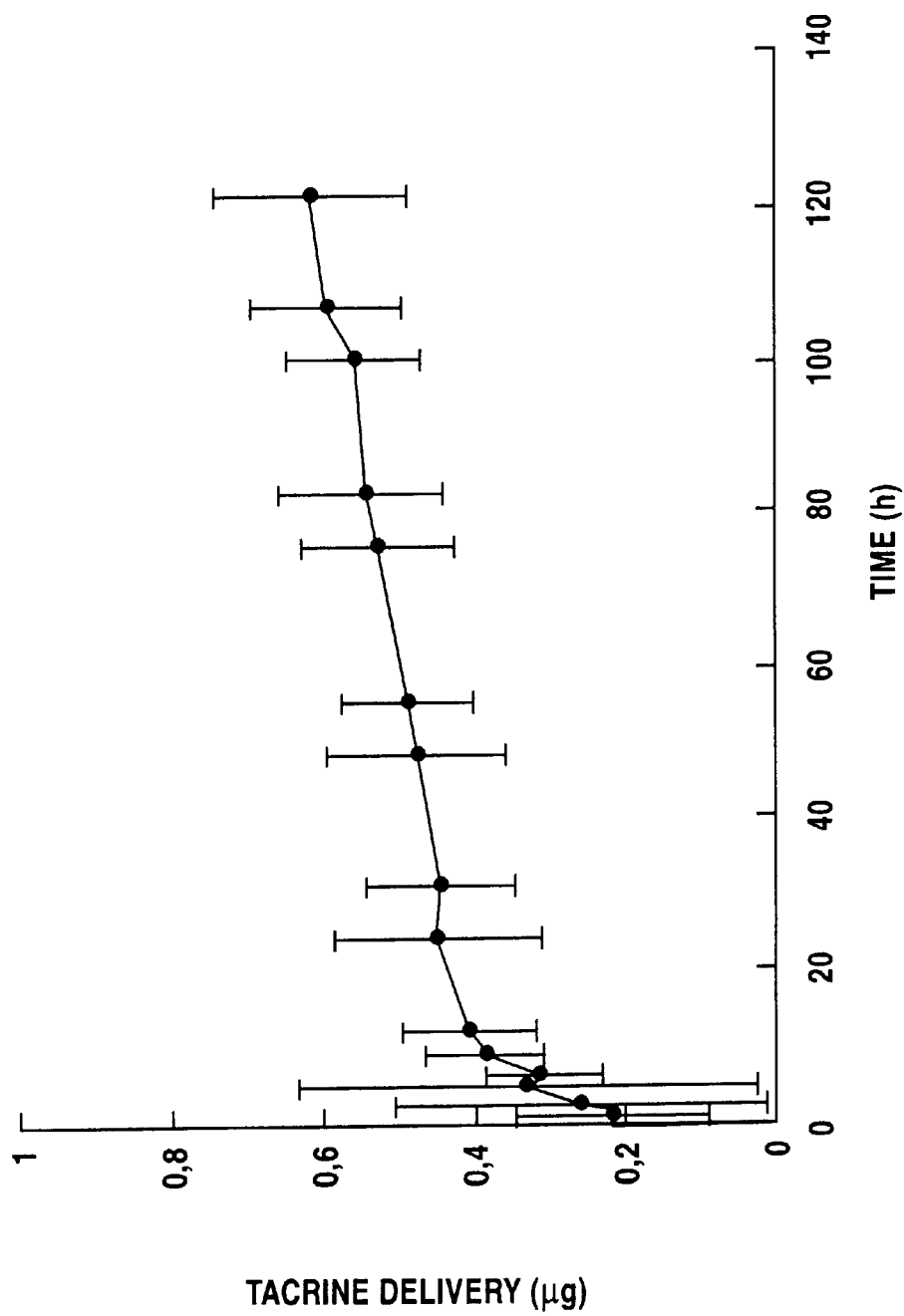
FIG. 7 shows tacrine permeation from a cationic ion-exchange fiber across human skin in vitro. Average±SD, N=7.

Human skin carries a net negative charge at neutral and basic pH (Burnette, 1989) and, therefore, the skin may "enhance" the permeation of positive tacrine. Transdermal permeation of tacrine across human skin at pH 7,4 is presented in FIG. 6. Steady-state flux of tacrine (5% solution) across human skin in vitro was 2,95 g/h per cm$^2$. Lag-time of permeation was long, ca. 24 h, until tacrine had penetrated through the skin into the receiver phase (FIG. 6). Delivery of tacrine across the skin from the cationic ion-exchange fiber was very low, about 0,003 g/h per cm$^2$ (FIG. 7). Drug delivery from the fiber was constant for 120 h, but the permeation rate of tacrine was about three orders of magnitude lower than in the case of tacrine solution. This implies that tacrine "prefers" the ion-exchange fiber over the skin as a permeation "target".

It will be appreciated that the compositions of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

Brain K R, Hadgraft J. James V J, Shah V P, Walters K A, Watkinson A C: In vitro assessment of skin permeation from a transdermal system for the delivery of oestradiol. Int J Pharm 89:R13–R16, 1993

Guy R H, Hadgraft J.: Transdermal drug delivery: a perspective. J Contr Rel 4: 237–251, 1987

Guy R H, Hadgraft J: Selection of drug candidates for transdermal drug delivery. In Transdermal Drug Delivery. pp. 59-81. Eds. Hadgraft J, Guy R H, Narcel Dekker Inc., N.Y., 1989

Gynther J: Lääkeainekemian perusteet. Fortis, Graafiset palvelut, Kuopio, 1993

Hirvonen J: Enhancement of transdermal drug penetration with dodecyl N, N-dimethylamino acetate and iontophoresis. Academic Dissertation, University of Kuopio, 1994

Sathyan G et al., Transdermal delivery of tacrine: I. Identification of a suitable delivery vehicle. Int.J.Pharm., 114:75–83, 1995

Wagstaff A J and McTavish D: Tacrine: A review of its pharmacodynamic and pharmacokinetic properties, and therapeutic efficacy in Alzheimer's disease. Drugs and Aging, 4: 510–540, 1994.

What is claimed is:

1. A transdermal pharmaceutical composition for the controlled transdermal delivery of a drug comprising a combination of a drug and a ion exchanger group grafted to a carrier, and a pharmaceutically acceptable salt that is able to control the release of the drug from the ion exchanger wherein the carrier is a non-crosslinked textile fiber, wherein said drug is present in an amount sufficient to ensure a daily dose of 30 mg or less.

2. The transdermal pharmaceutical composition according to claim 1 wherein the textile fiber is selected from the group consisting of wool, cotton, flax fibers and fibers of cellulose or its derivatives, polyethylene, polypropylene, polystyrene, polyamide fibers and carbon fibers.

3. The transdermal pharmaceutical composition according to claim 1 wherein a cation has been grafted to the fiber.

4. The transdermal pharmaceutical composition according to claim 1 wherein an anion has been grafted to the fiber.

5. The transdermal pharmaceutical composition according to claim 3 wherein the fiber is a cotton fiber to which a tertiary amine cation -$N^+(CH_3)_3$ has been grafted.

6. The transdermal pharmaceutical composition according to claim 1, wherein the textile fiber is a woven cloth.

7. The transdermal pharmaceutical composition according to claim 1, wherein the pharmaceutically acceptable salt is encompassed in a gel which is brought into contact with the textile fiber.

8. The transdermal pharmaceutical composition according to claim 7 characterized in that the gel is brought into contact with only one surface of the textile cloth.

9. The transdermal pharmaceutical composition according to claim 7 characterized in that the textile fiber is immersed in the gel.

10. The transdermal pharmaceutical composition according to any one of the previous claims characterized in that the drug is tacrine or its pharmaceutically acceptable salt.

* * * * *